(12) United States Patent
Chang et al.

(10) Patent No.: US 12,263,283 B1
(45) Date of Patent: Apr. 1, 2025

(54) WEARABLE DEVICES THAT ACTIVELY DISINFECT

(71) Applicant: Huei Meng Chang, Milpitas, CA (US)

(72) Inventors: Huei Meng Chang, Milpitas, CA (US); Phong D. Pham, Union City, CA (US); Leo Y. Kwok, Milpitas, CA (US); Isaac E Chang, Milpitas, CA (US)

(73) Assignee: Huei Meng Chang, Milpitas, CA (US)

( * ) Notice: Subject to any disclaimer, the term of this patent is extended or adjusted under 35 U.S.C. 154(b) by 943 days.

(21) Appl. No.: 17/366,060

(22) Filed: Jul. 2, 2021

Related U.S. Application Data

(60) Provisional application No. 63/047,278, filed on Jul. 2, 2020.

(51) Int. Cl.
| | | |
|---|---|---|
| *A61L 9/20* | (2006.01) | |
| *A41D 13/11* | (2006.01) | |
| *A62B 18/00* | (2006.01) | |

(52) U.S. Cl.
CPC ............. *A61L 9/20* (2013.01); *A41D 13/11* (2013.01); *A62B 18/003* (2013.01); *A61L 2209/14* (2013.01); *A61L 2209/15* (2013.01)

(58) Field of Classification Search
CPC ....... A61L 9/20; A61L 2209/14; A41D 12/11; A41D 13/11
See application file for complete search history.

(56) References Cited

U.S. PATENT DOCUMENTS

| | | | |
|---|---|---|---|
| 7,658,891 B1* | 2/2010 | Barnes | C01B 13/11 128/205.28 |
| 2015/0114397 A1* | 4/2015 | Litz | A62B 19/00 128/206.15 |
| 2019/0117820 A1* | 4/2019 | Dam | B03C 3/32 |
| 2019/0357625 A1* | 11/2019 | Chen | A42B 3/16 |

* cited by examiner

*Primary Examiner* — Donald R Spamer

(57) ABSTRACT

A wearable device takes potentially contaminated air from the environment, sterilizes it with UVC light, and transports the sterilized air to a headgear. In the headgear it provides an air curtain at a slight overpressure, flowing from the top down. Used air exits the headgear at its bottom. The headgear includes a helmet or a full-face mask. An inline system connects to the headgear using an air hose. The inline system has two or more connecting pipes on the inside of which are UVC light sources. Air flows from an air inlet filter through the connecting pipes, where it is disinfected by the UVC light, to the air hose and headgear. Mounting brackets mount the connecting pipes, and may include fans, and brackets for the UVC light sources.

13 Claims, 19 Drawing Sheets

WEARABLE DEVICES THAT ACTIVELY DISINFECT

CROSS REFERENCES

This application claims priority from U.S. Provisional Patent Application Ser. No. 63/047,278, entitled "Methods and Apparatuses for Wearable Device that Actively Disinfect Bacteria and Viruses", filed on Jul. 2, 2020, which is hereby incorporated by reference as if set forth in full in this application for all purposes.

Each publication, patent, and/or patent application mentioned in this specification is herein incorporated by reference in its entirety to the same extent as if each individual publication and/or patent application was specifically and individually indicated to be incorporated by reference.

BACKGROUND

Technical Field

The disclosed embodiments relate generally to tools and methods used in disinfecting contagious environments.

Context

Unless otherwise indicated herein, elements described in this section are not prior art to the claims and are not admitted being prior art by inclusion in this section.

Frontline workers in contagious environments face daily risks for their own health, and their need for reliable and safe personal protective equipment (PPE) is high. Many pathogens spread through the air, making disinfection of air to breathe a high priority. Ultraviolet light, especially UVC light, is known for its disinfecting capabilities, but has been lacking in PPE. Some have tried, but come up short in providing an easy to use system that provides safe breathable air.

SUMMARY

Embodiments of the invention provide a wearable device that sterilizes air and provides safety to frontline workers. The wearable device takes potentially contaminated air from the environment, sterilizes it with UVC light, and transports the sterilized air to a headgear. In the headgear it provides an air curtain at a slight overpressure, flowing from the top down. Used air exits the headgear at its bottom.

In an aspect of the invention, the wearable device includes a headgear and an inline system, coupled by an air hose that transports sterilized air from the inline system to the headgear. The inline system has two end mounting brackets. One of the end mounting brackets couples to the air hose. The other end mounting bracket has an air inlet filter. Both end mounting brackets hold one of two connecting pipes. Each connecting pipe holds a UVC light source inside. Potentially contaminated air enters the air inlet filter. It is pushed or sucked (by a fan) into the connecting pipes, where it is disinfected. The disinfected air travels through the air hose to the head gear.

The headgear may include a helmet or a full-face mask.

The inline system may further include a u-shaped backpack to couple the connecting pipes. The u-shaped backpack may include a fan, and may include a bracket to hold one of the UVC light sources. Alternatively, the inline system may include two connecting mounting brackets and a bridging bracket. The bridging bracket couples the two connecting mounting brackets to each other. The connecting mounting brackets couple with the connecting pipes. The connecting mounting brackets may also include a fan, and include a bracket to hold one of the UVC light sources.

Both the u-shaped backpack and the connecting mounting brackets enable the connecting pipes to be anti-parallel oriented, to allow for a greater effective length without the inline system becoming impractical.

A further understanding of the nature and the advantages of particular embodiments disclosed herein may be realized by reference of the remaining portions of the specification and the attached drawings.

BRIEF DESCRIPTION OF THE DRAWINGS

The invention will be described with reference to the drawings, in which.

In the figures, like reference numbers may indicate functionally similar elements. The systems and methods illustrated in the figures, and described in the Detailed Description below, may be arranged and designed in a wide variety of different embodiments. Neither the figures, nor the Detailed Description, are intended to limit the scope as claimed. Instead, they merely represent examples of different embodiments of the invention.

DETAILED DESCRIPTION

Terminology

As used herein, the term "and/or" should be interpreted to mean one or more items. For example, the phrase "A, B, and/or C" should be interpreted to mean any of: only A, only B, only C, A and B (but not C), B and C (but not A), A and C (but not B), or all of A, B, and C. As used herein, the phrase "at least one of" should be interpreted to mean one or more items. For example, the phrase "at least one of A, B, and C" or the phrase "at least one of A, B, or C" should be interpreted to mean any of: only A, only B, only C, A and B (but not C), B and C (but not A), A and C (but not B), or all of A, B, and C. As used herein, the phrase "one or more of" should be interpreted to mean one or more items. For example, the phrase "one or more of A, B, and C" or the phrase "one or more of A, B, or C" should be interpreted to mean any of: only A, only B, only C, A and B (but not C), B and C (but not A), A and C (but not B), or all of A, B, and C.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

UV—Ultraviolet light is electromagnetic radiation with wavelengths from 100 to 405 nm. The UV band is divided into three sections: UVA (315-400 nm), UVB (280-315 nm) and UVC (100-280 nm).

UVC, a subset of UV light, has a range of wavelengths from 100 nm to 280 nm. It was discovered in 1877 that UVC in sunlight was highly effective at disinfecting. It was subsequently discovered to be both effective at inactivating both bacteria and viruses.

EMBODIMENTS

Figure 1:
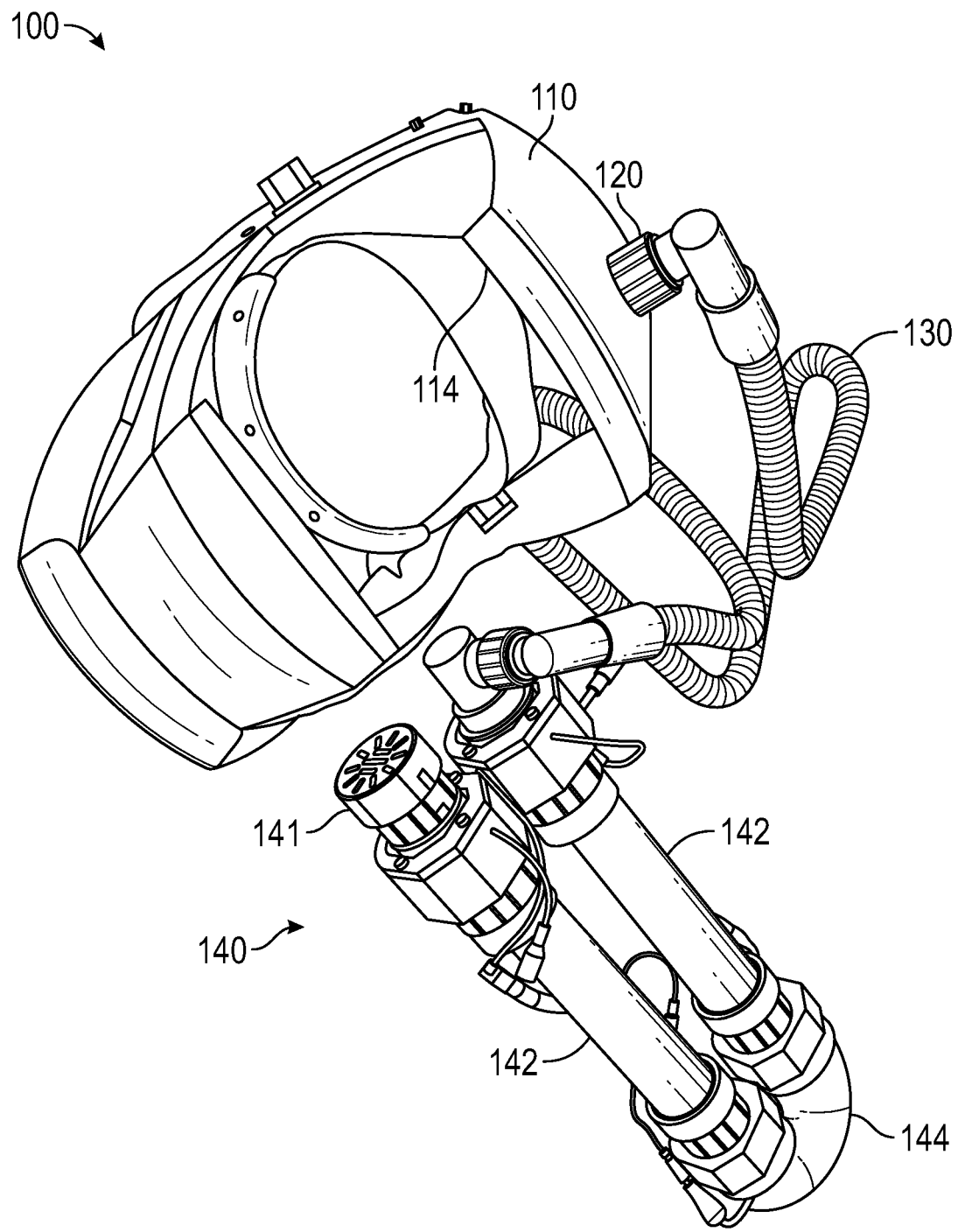
FIGS. 1 and 1A illustrate a wearable device with headgear according to an embodiment of the invention.

FIG. 1 illustrates a wearable device 100 with headgear 110 according to an embodiment of the invention. Wearable device 100 includes headgear 110, which may comprise a helmet or a face mask, air hose 130 which connects headgear 110 to an inline system 140 comprising air inlet filter 141, connecting pipes 142 and u-shaped backpack 144. Headgear 110 is shaped in such a manner that when worn, air enters via a sterilized air intake 120, which is used for connecting air hose 130. An embodiment maintains a slight positive air pressure inside headgear 110 to minimize risk of any contaminated air entering headgear 110. Wearable device 100 also has an option to provide a continuous flow of sterilized air like an air curtain in the immediate vicinity of a user's face, originating at the top of visor 114, inside headgear 110. Inline system 140 receives fresh, but potentially contaminated air via air inlet filter 141, pumps the air through connecting pipes 142, and sterilizes it by killing or deactivating all biological contaminants through exposure to UVC light. U-shaped backpack 144 may house fans, brackets to hold the UVC light sources, various sensors, and any cooling systems.

Figure 1A:
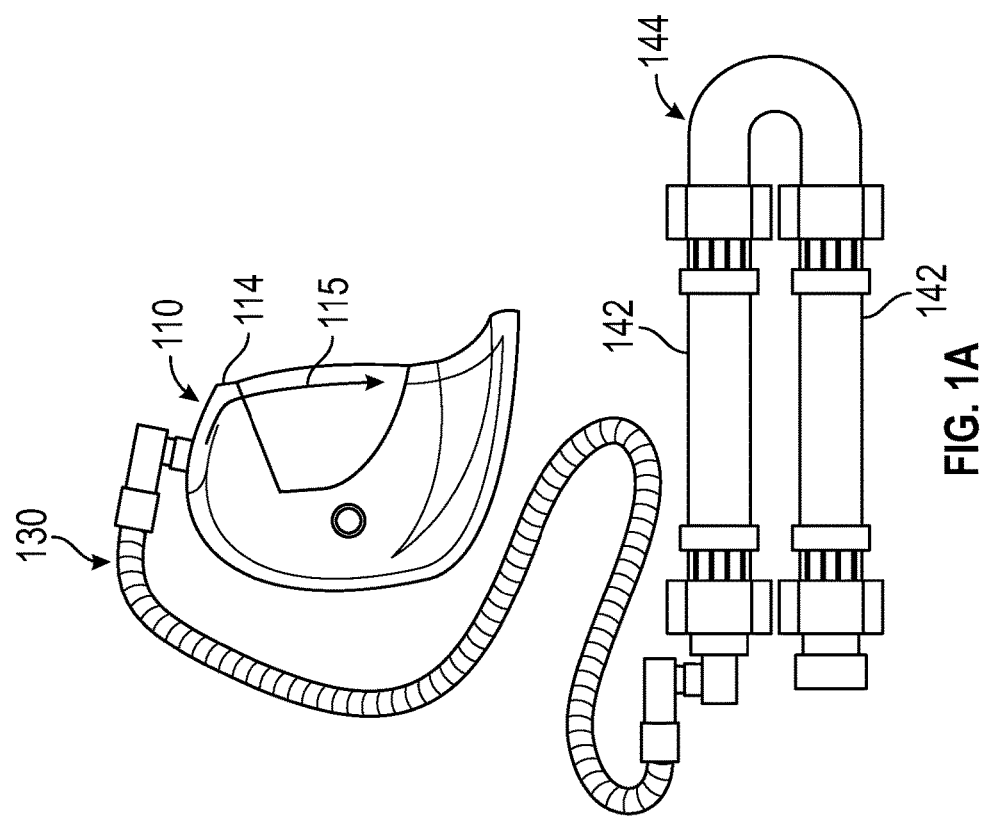

One or more fans in inline system 140 pump the sterilized air into air hose 130 from which it enters headgear 110 at sterilized air intake 120. Inside headgear 110, the airflow provides the air curtain flowing from the top of visor 114 and the top of the user's face to the bottom of the headgear, where either an air gap or an air outlet filter with optional fan releases used air to the surroundings. FIG. 1A provides a sectional view, with the sterilized air entering headgear 110 at the top, and being guided to the front, where from the top of visor 114 it flows down to provide the air curtain 115.

Figure 2:
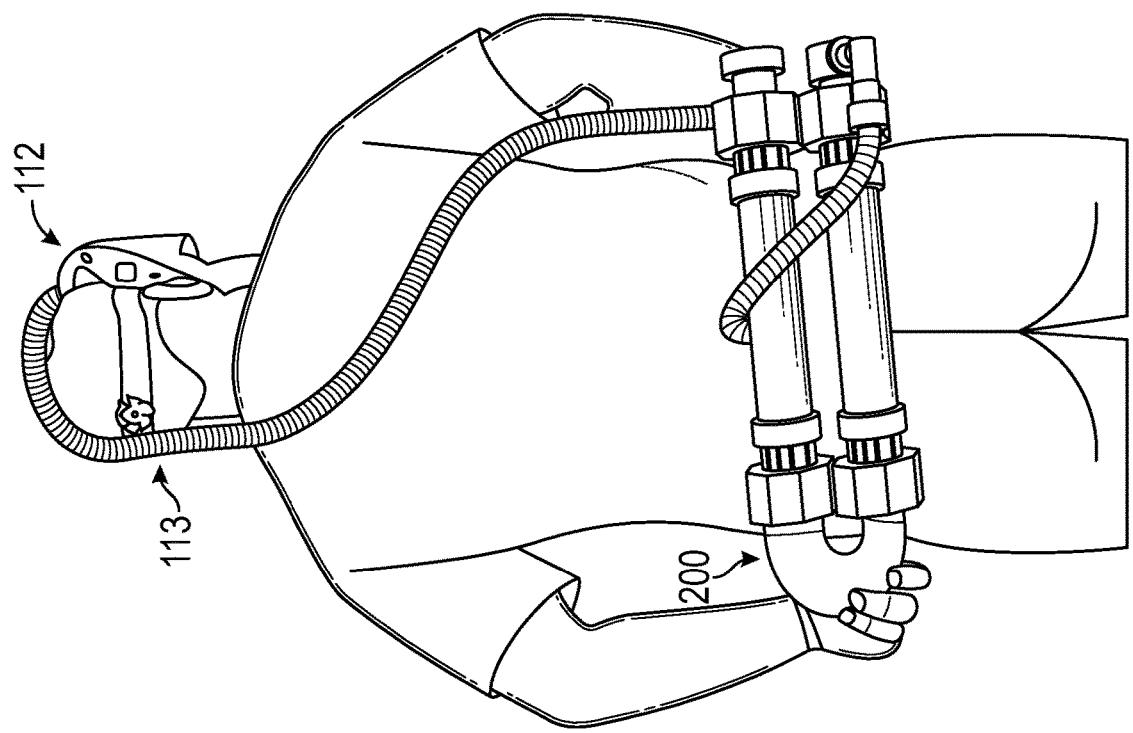
FIG. 2 illustrates an example usage of the wearable device of FIG. 1.

FIG. 2 illustrates an example usage of the wearable device 100 of FIG. 1. The example shows a user from the back. The user wears headgear 110 over his head and face. Air hose 130 runs along his body from headgear 110 to inline system 140, which in this example he carries low on his back 200.

Figure 3A:
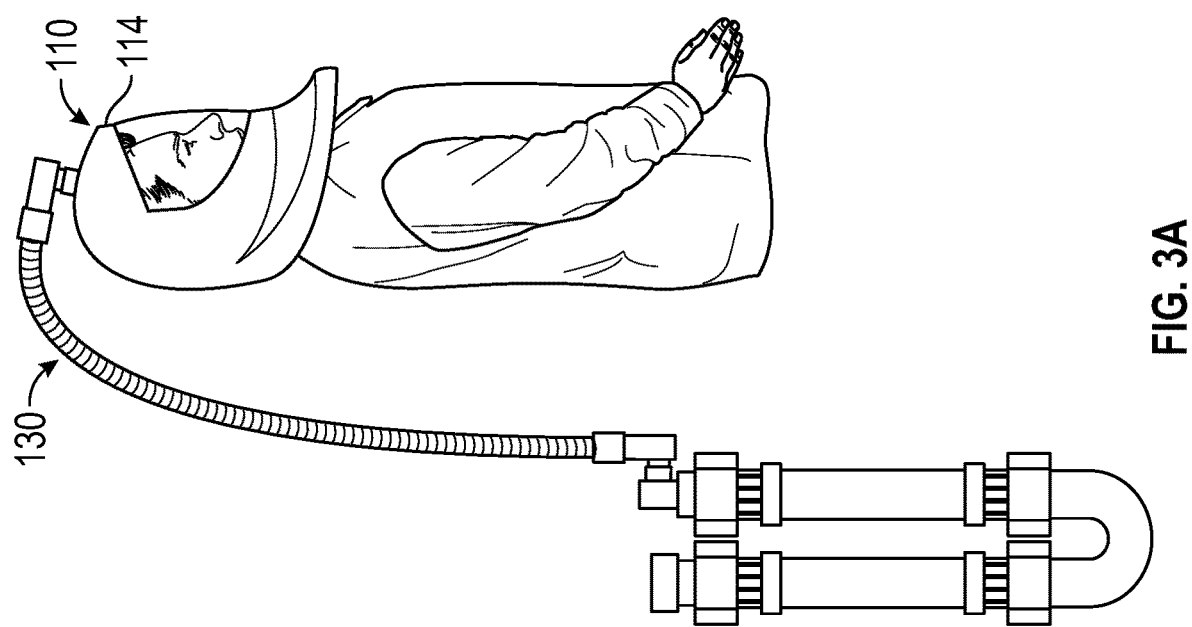
FIGS. 3 and 3A illustrate another example usage of wearable device of FIG. 1.
Figure 3:
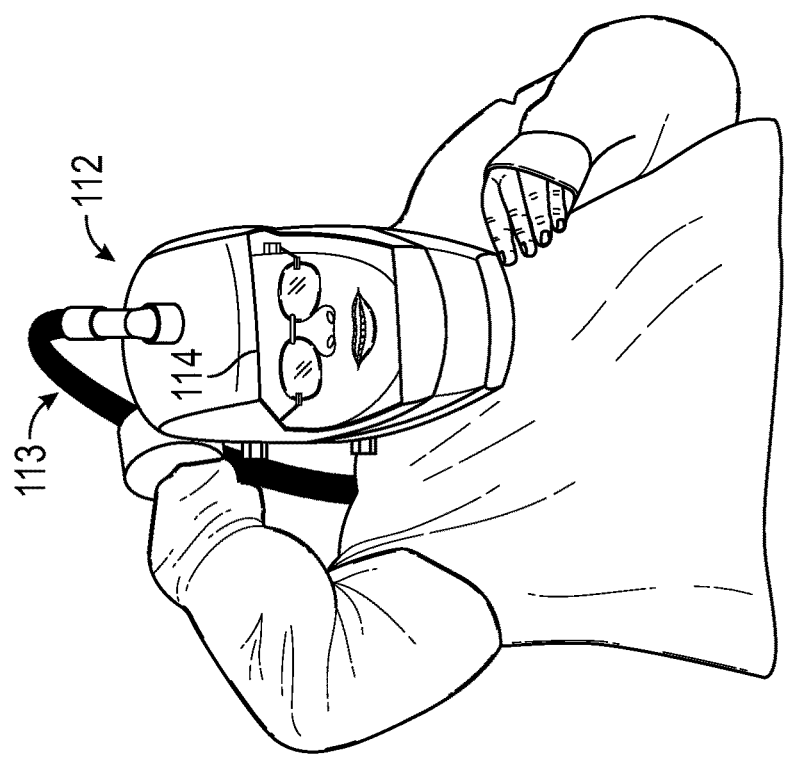

FIG. 3 illustrates another example usage of wearable device 100 of FIG. 1. This example shows a user from the front. FIG. 3A shows a sideview.

Figure 4:
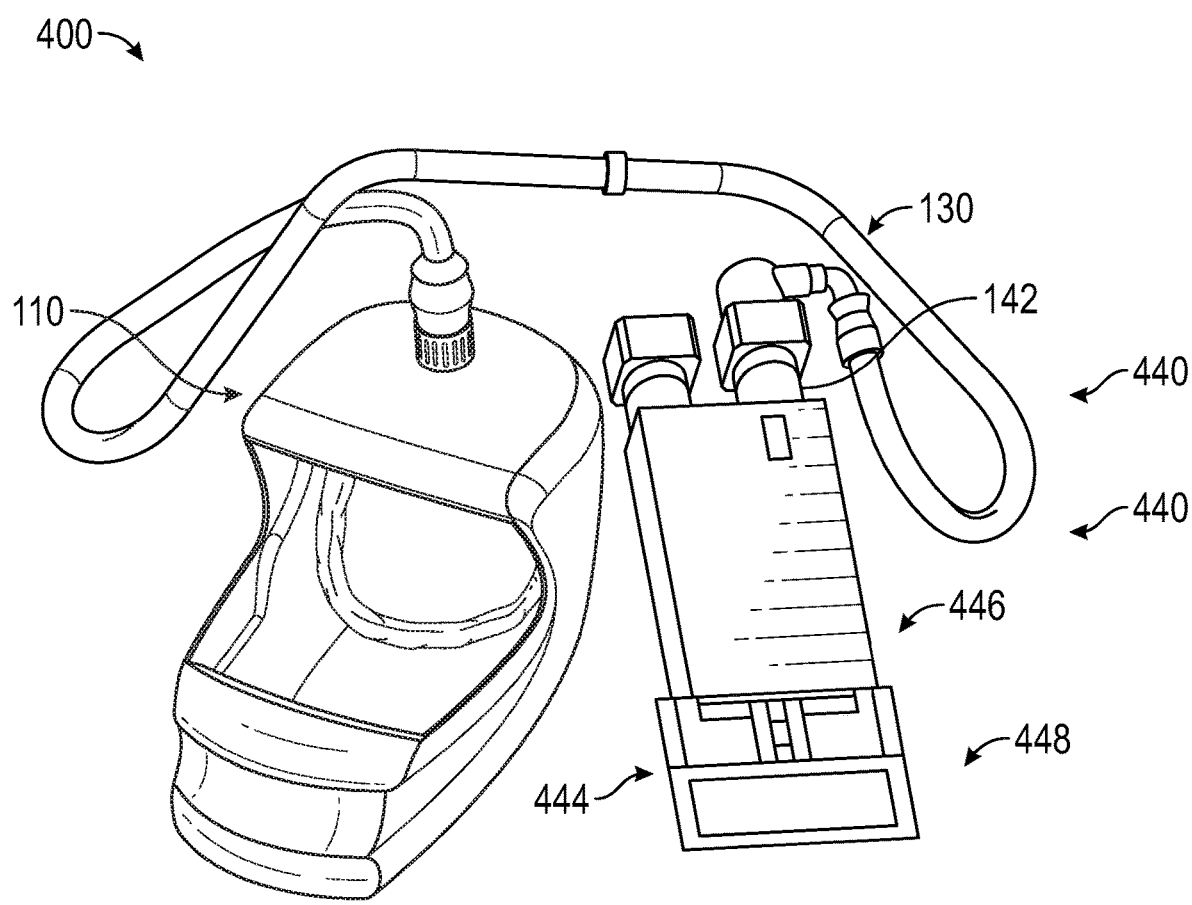
FIG. 4 illustrates a wearable device including a waist pack according to an embodiment of the invention.

FIG. 4 illustrates a wearable device 400 including a waist pack according to an embodiment of the invention. Wearable device 400 comprises headgear 110, air hose 130 and inline system 440. Inline system 440 includes connecting pipes 142, waist pack 444, power and electronics pack 446 and portable display 448. Power and electronics pack 446 is field accessible and removable. It is designed to be hot swapped. In some embodiments, power and electronics pack 446 includes a rechargeable battery and a charger and can be coupled to an external power supply, for instance a mains outlet, via an extension cord. It may further include ballasts for UVC lamps (described later, and also dependent on the lamp type(s)), and control electronics to regulate the airflow as required by a user's breathing patterns. Portable display 448 shows system information including, but not limited to, the battery status, battery usage, fan status, general air quality, and options for various quality measurements including CO2, ozone, and others.

Figure 5:
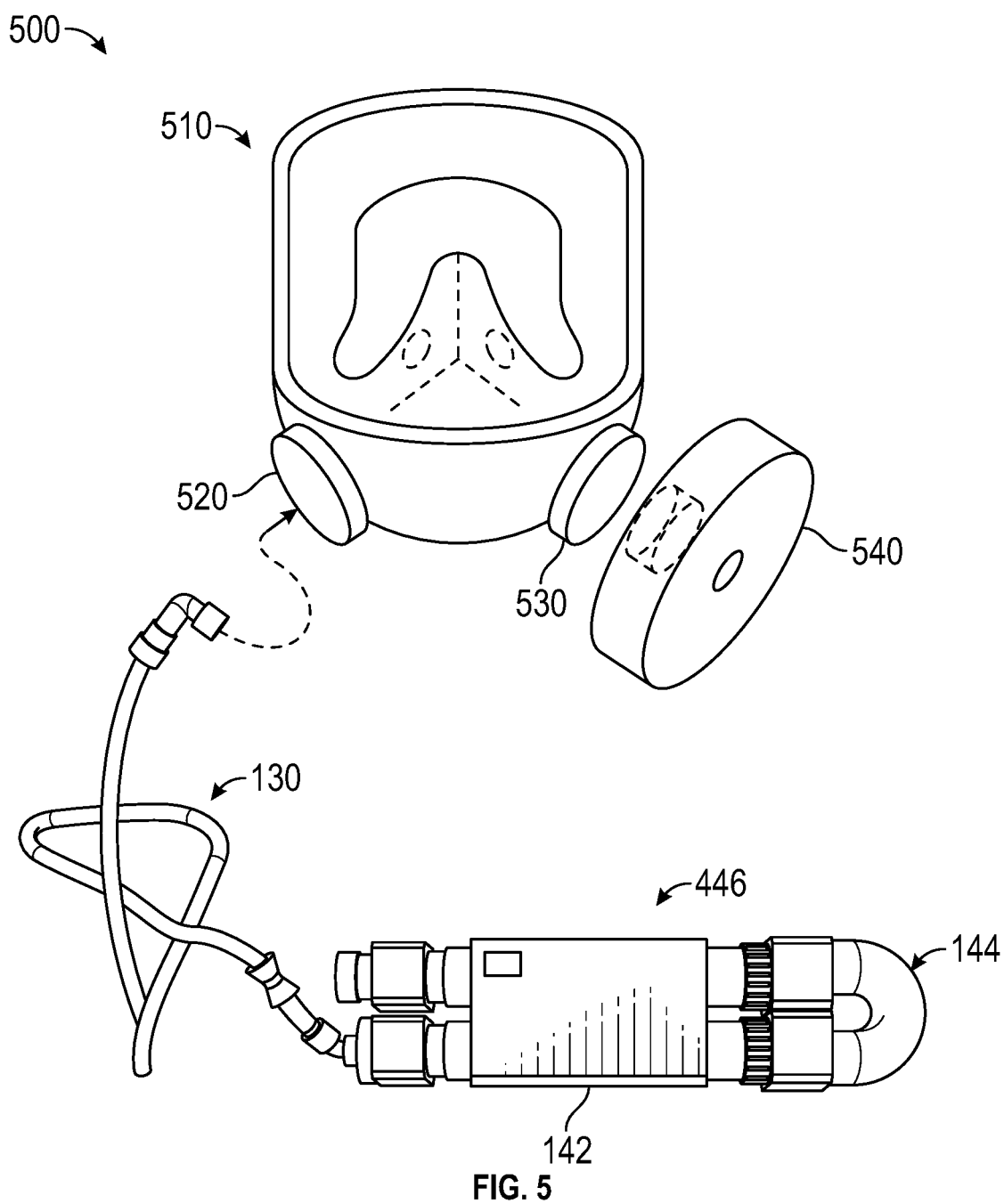
FIG. 5 illustrates a wearable device with a full face mask according to an embodiment of the invention.

FIG. 5 illustrates a wearable device 500 with a full face mask 510 according to an embodiment of the invention. Full face mask 510 comprises sterilized air intake 520 and air exhaust 530 which, as drawn, couples with an exhalation valve 540 that may include a filter. Full face mask 510 is sealed from ambient air, so that all air enters via u-shaped backpack 144, connecting pipes 142, and sterilized air intake 520, and exits via air exhaust 530.

Figure 6:
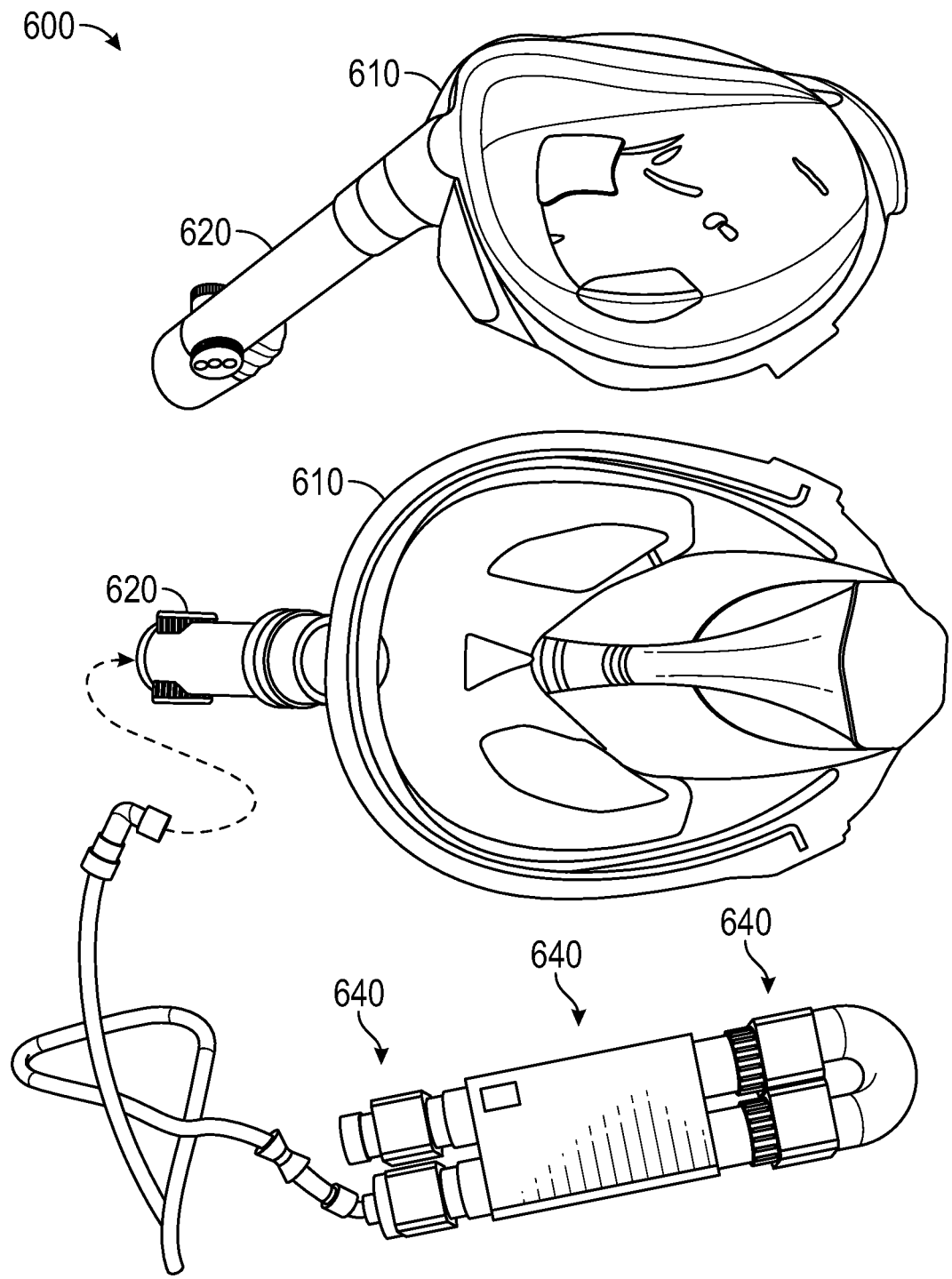
FIG. 6 illustrates another wearable device with a full face mask according to an embodiment of the invention.

FIG. 6 illustrates another wearable device 600 with a full face mask 610 according to an embodiment of the invention. Wearable device 600 further includes inline system 640. Full face mask 610 resembles a full-face snorkel mask which is modified to provide a full-face shield and air seal. It allows for controlled intake and exhaust flows through the mask via sterilized air intake 620. Inline system 640 sterilizes the respiration airflow by killing or deactivating all biological contaminants through exposure to UVC light.

Figure 7:
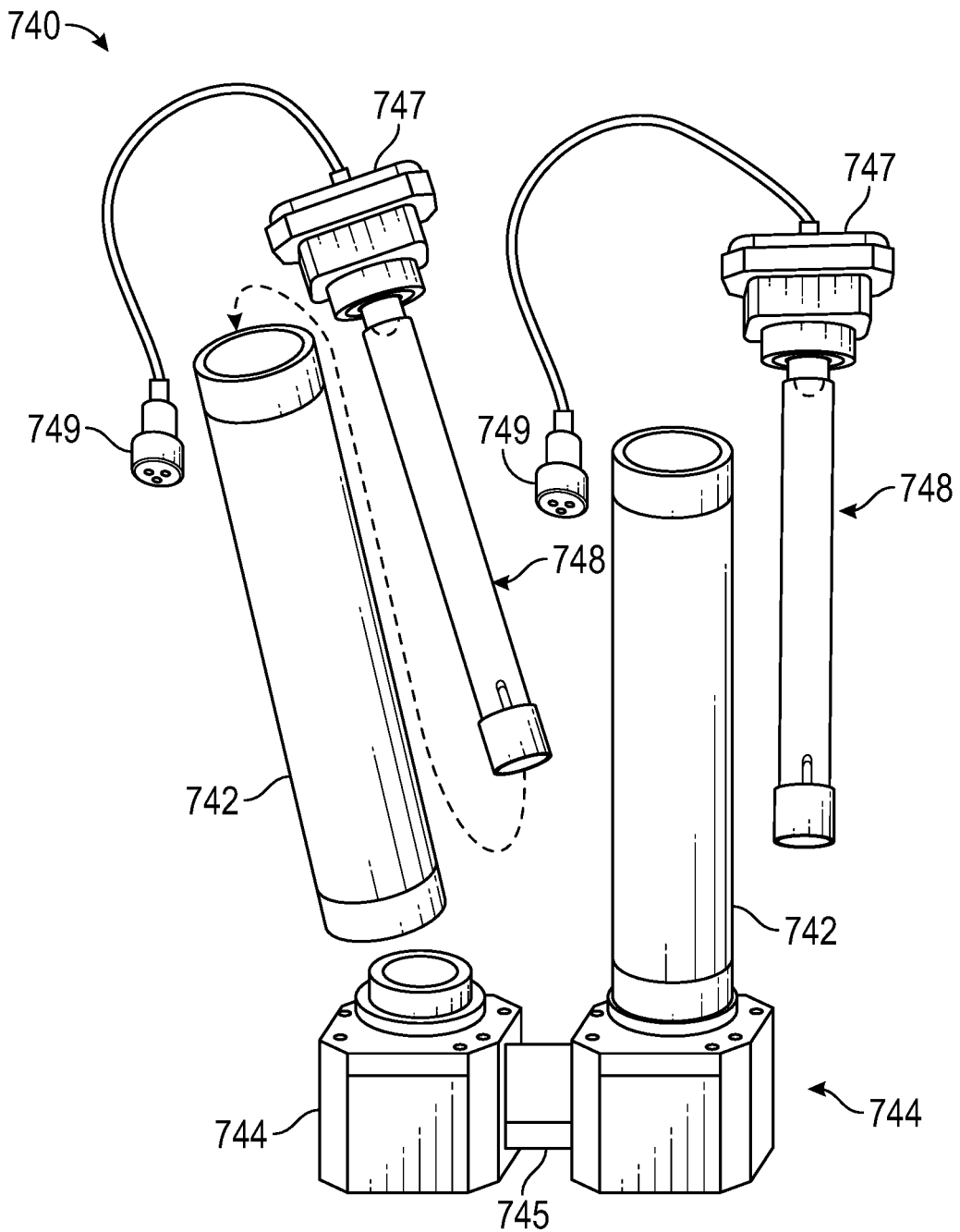
FIG. 7 illustrates details of an inline system according to an embodiment of the invention.

FIG. 7 illustrates details of an inline system 740 according to an embodiment of the invention. Inline system 740 comprises connecting pipes 742, connecting mounting brackets 744, bridging bracket 745, end mounting brackets 747, and UVC lamps 748. Each of the connecting pipes 742 is mounted between one of the connecting mounting brackets 744 and one of the end mounting brackets 747. Each of the end mounting brackets 747 holds one of the UVC lamps 748, in such a way that when the connecting pipes 742 are mounted in the end mounting brackets 747, the UVC lamps 748 are placed inside the connecting pipes 742. In some embodiments, connecting pipes 742 are made of lightweight PVC pipe, whose inside surface is lined with reflective material, for example aluminum foil or coating. In other embodiments, connecting pipes 742 are made of a metal, such as aluminum, and their insides are naturally reflective. In yet other embodiments, connecting pipes 742 may be made of any lightweight material. In an example embodiment, connecting pipes 742 have a length of 1.5 feet and a diameter of 1.5 to 3 inches. In other embodiments, connecting pipes 742 may have different lengths and/or diameters.

Bridging bracket 745 provides for a mechanical coupling between the two connecting mounting brackets 744. It is hollow, and allows for airflow to pass from within the inside of one of the connecting pipes 742 to another.

UVC lamps 748 are powered by the power pack (not shown), and—for some types of lamps—they may electrically couple to ballast devices via connectors 749. Lamp types include, but are not limited to, low-pressure and medium-pressure mercury lamps, low-pressure amalgam lamps, excimer lamps, and LEDs. Different lamps may have different peak wavelengths, and therefore be suitable for protection against different types of biological agents. UVC lamps 748 may be in the range of 9 to 13 Watts, but an embodiment may also include a higher or lower power UVC lamp or LED strip.

Figure 8:
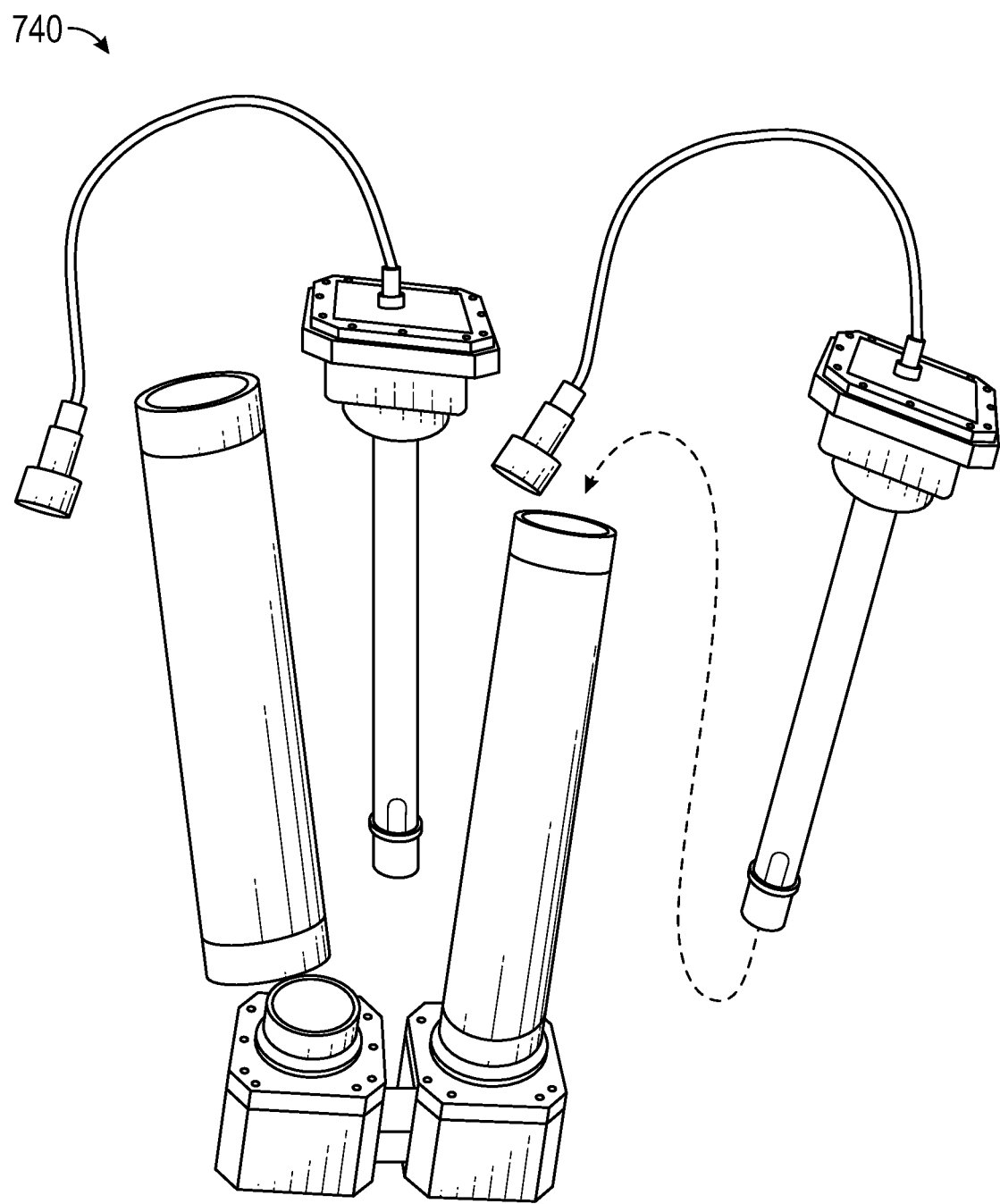
FIG. 8 illustrates the inline system from a different perspective.

FIG. 8 illustrates inline system 740 from a different perspective.

Figure 9:
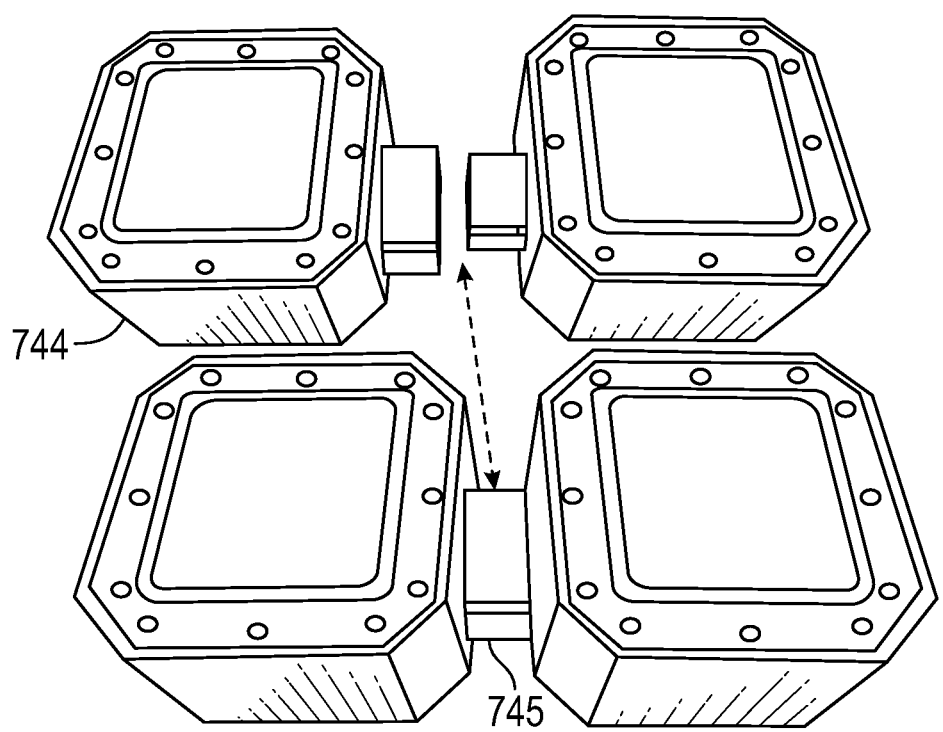
FIG. 9 illustrates further details of the connecting mounting brackets and bridging bracket according to an embodiment of the invention.

FIG. 9 illustrates further details of the connecting mounting brackets 744 and bridging bracket 745 according to an embodiment of the invention. In this embodiment, bridging bracket 745 is divided in two parts, one on each mounting bracket. One part can slide in the other, with a snug fit to provide robust coupling. The airflow may go through the inner part.

Figure 10:
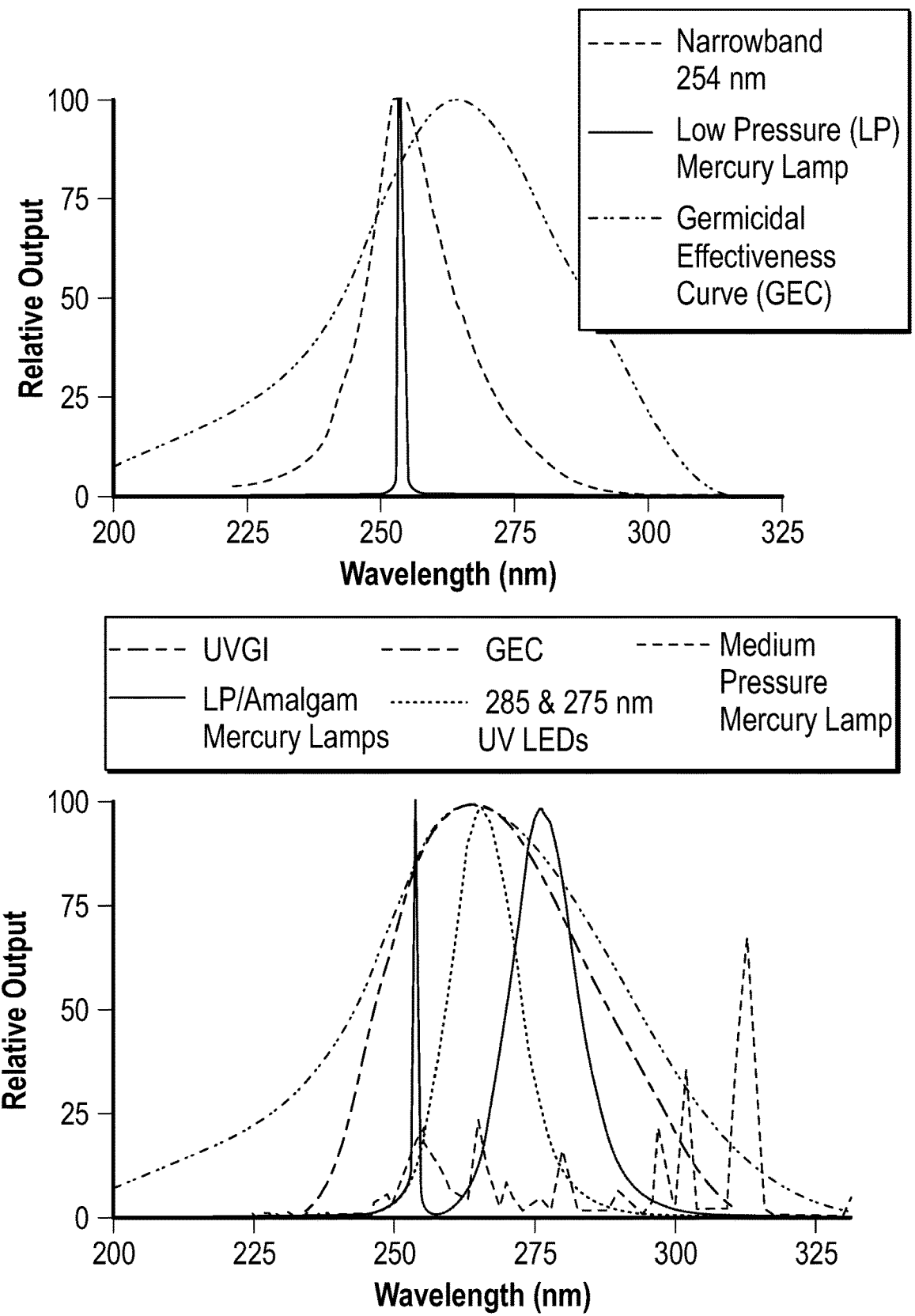
FIGS. 10-11 show the relative outputs versus the peak wavelengths for existing UV light sources with various peak wavelengths.
Figure 11:
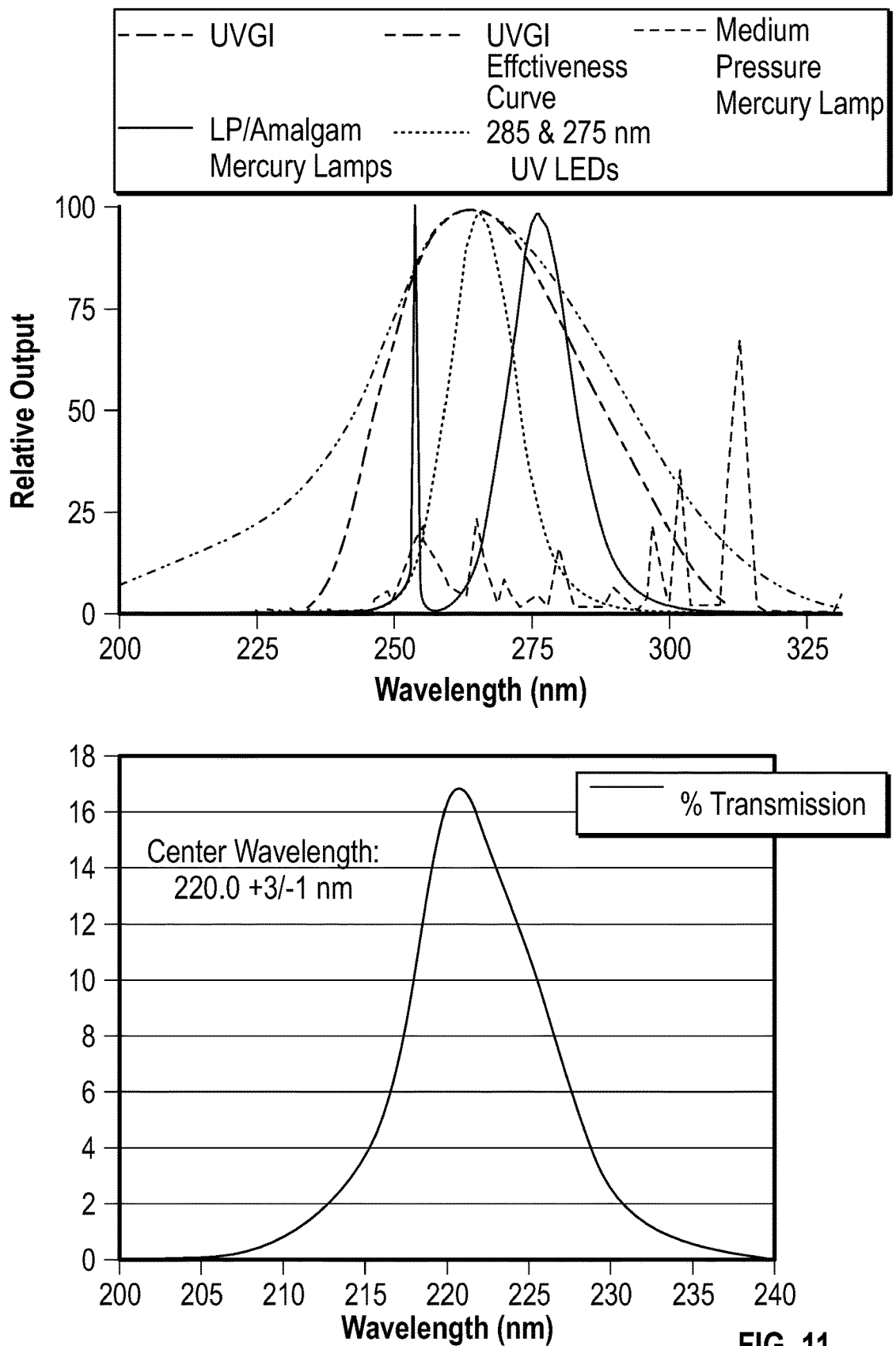

FIGS. 10-11 show the relative outputs versus the peak wavelengths for existing UV light sources with various peak wavelengths. A Germicidal Effectiveness Curve (GEC) peaks at around 270 nm, indicating that, for example, an embodiment with 275 nm UVC LEDs will be most effective, and even low-pressure mercury lamps, medium-pressure mercury lamps, and 285 nm UC LEDs will be very effective. Embodiments of the invention may employ any light sources whose peak wavelengths are above 220 nm and below 300 nm, or whose peak wavelengths are suited to sterilize any particular biological contaminant.

Figure 12:
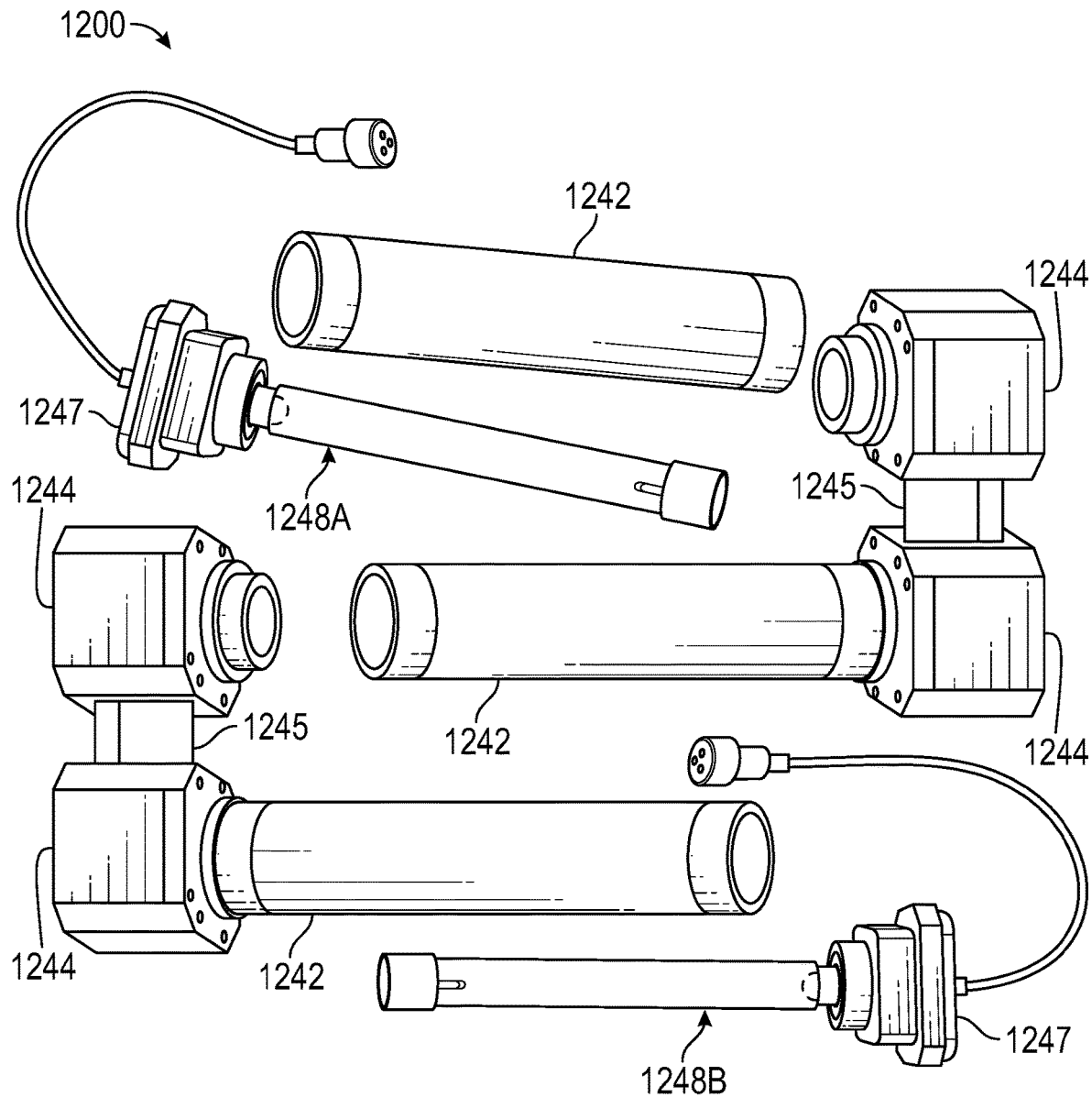
FIG. 12 illustrates an inline system with three segments according to an embodiment of the invention.

FIG. 12 illustrates an inline system 1200 with three segments according to an embodiment of the invention. Further embodiments may comprise even more segments. Each segment comprises a connecting pipe 1242 mounted in between two mounting brackets. Each connecting pipe 1242 envelopes a UVC light source 1248A-B mounted into at least one of the surrounding mounting brackets. Air flows through all segments, which are coupled to each other with bridge brackets 1245. Some embodiments may employ a single type of UVC light source 1248, whereas other embodiments employ two, three, or even more types of UVC light source 1248, so that the choice of type or types allows for optimizing the inline system 1200 UVC spectrum for any combination of biological contaminants that are of particular concern. Inline system 1200 includes connecting mounting brackets 1244 and two each of end mounting bracket 1247. An end mounting bracket 1247 is configured to couple with an air inlet filter or with an air hose. It may also be configured to let out wires for coupling with a power and electronics pack. Each of the connecting mounting brackets 1244 is configured to couple with another one of the connecting mounting brackets 1244 via one of the bridge brackets 1245. Both an end mounting bracket 1247 and one or more of the connecting mounting brackets 1244 may be configured to mount a UVC light source 1248.

Although FIG. 12 shows each end mounting bracket 1247 with an electric cord and connector for coupling to a power supply pack and/or ballast, some embodiments loop the power through all segments, so that a single electric cord and connector suffices for powering all UVC light sources.

Figure 13:
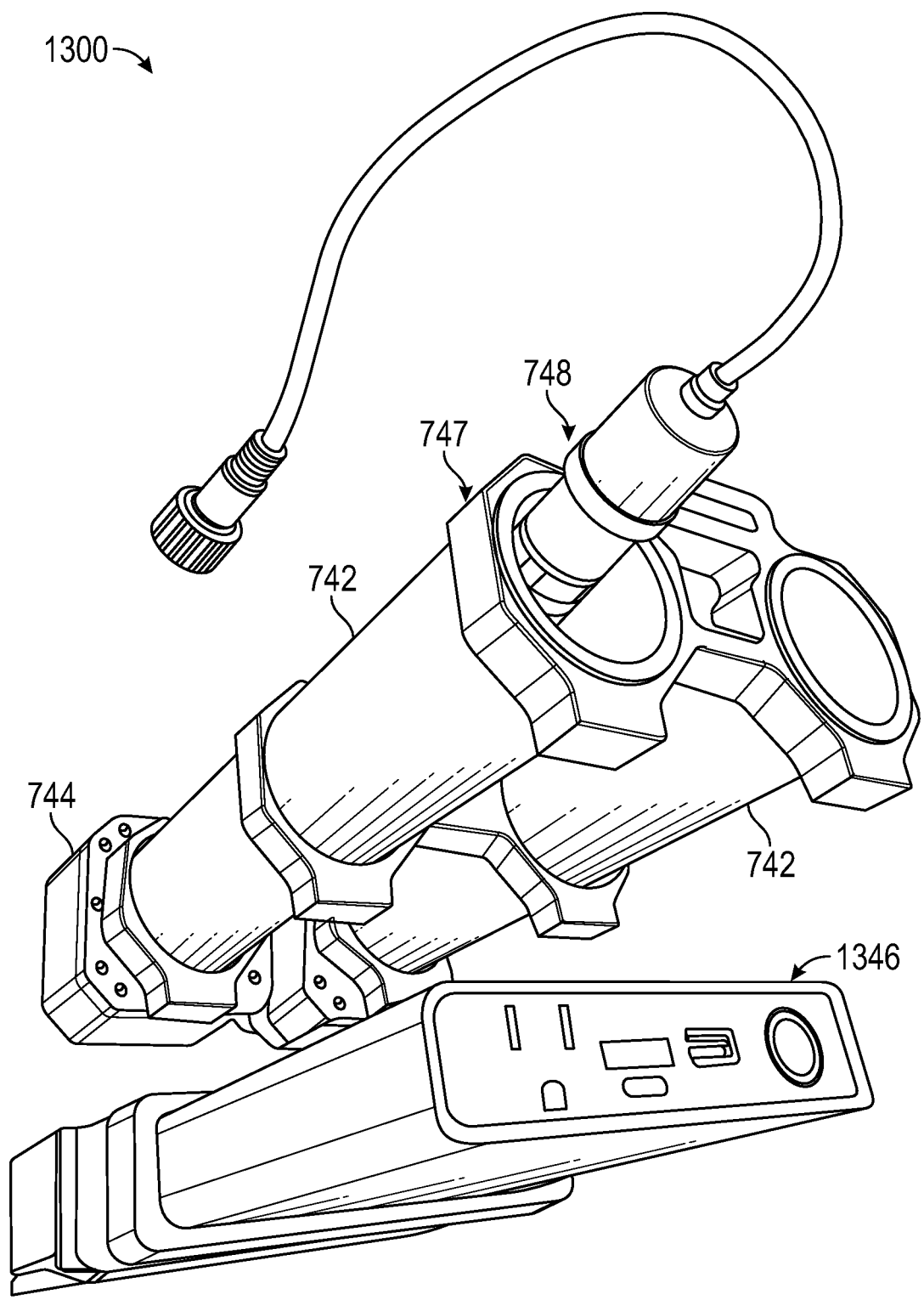
FIGS. 13-14 show perspectives of an example waist pack including a power supply and electronics pack according to an embodiment of the invention.
Figure 14:
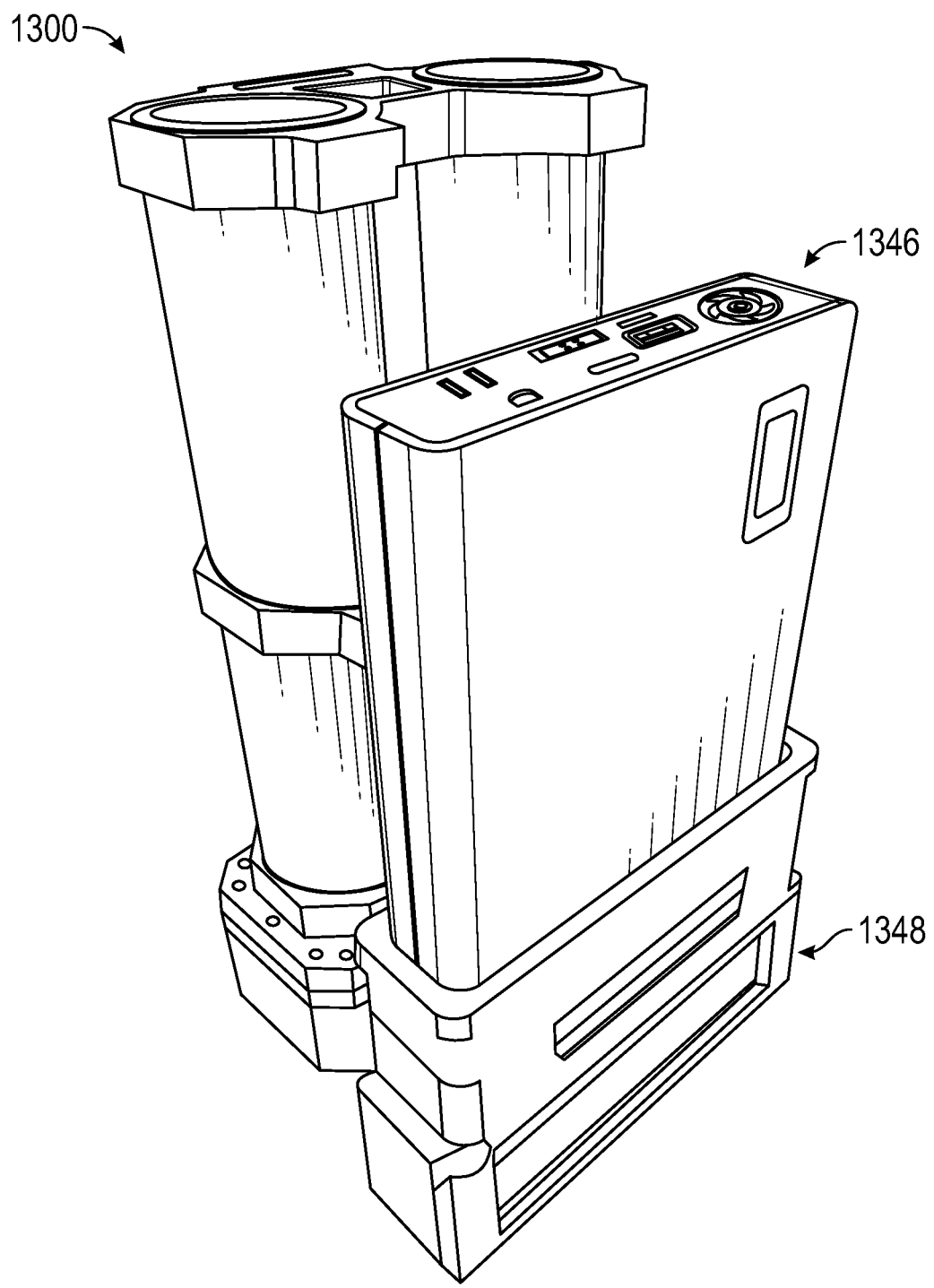

FIGS. 13-14 show perspectives of an example waist pack 1300 including a power supply and electronics pack 1346 according to an embodiment of the invention. Power supply and electronics pack 1346 mounts removably on waist pack 1300. FIG. 14 also shows example positioning of portable display 1348.

Figure 15:
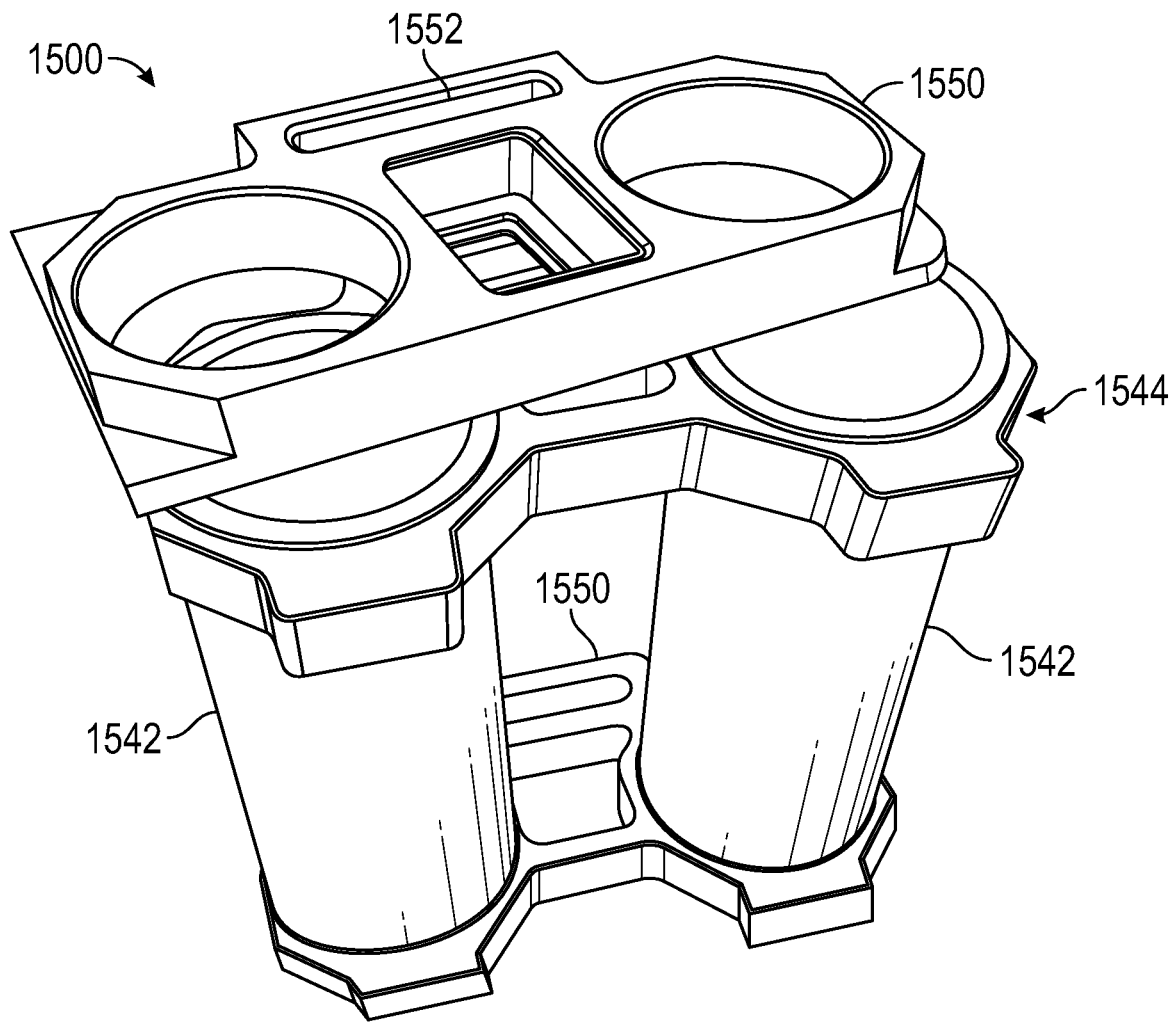
FIG. 15 illustrates a waist pack with belt holders according to an embodiment of the invention.

FIG. 15 illustrates a waist pack 1500 with belt holders 1550 according to an embodiment of the invention. FIG. 15 shows connecting pipes 1542 and mounting brackets 1544. Each of the belt holders 1550 has a belt slot 1552. The belt holders 1550 slide over and may snap to the connecting pipes 1542 so that the waist pack 1500 can be conveniently worn at the waist.

Figure 16:
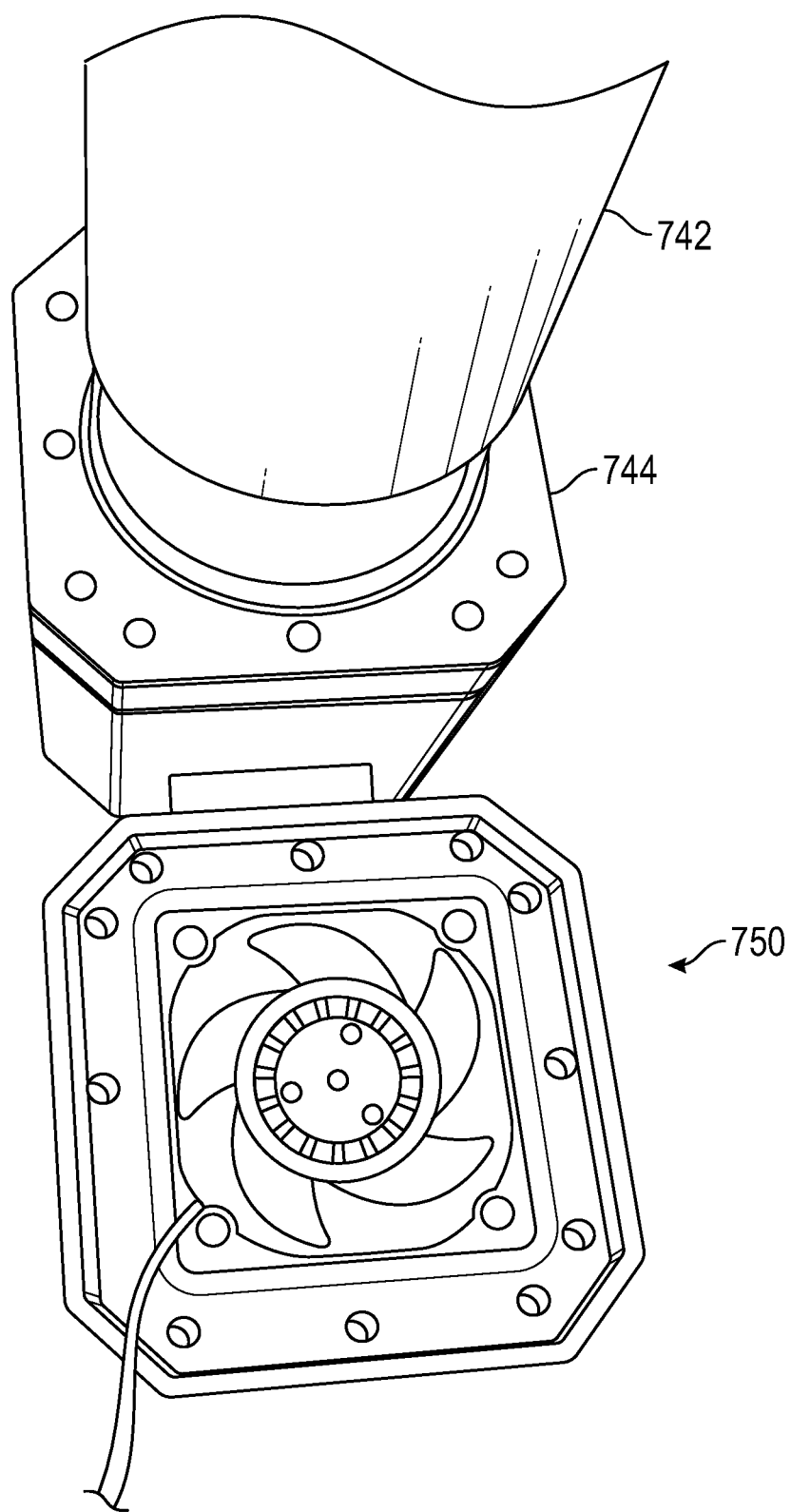
FIG. 16 illustrates how a rotational fan may be integrated in one (or more) of the connecting mounting brackets.

FIG. 16 illustrates how a rotational fan 750 may be integrated in one (or more) of the connecting mounting brackets 744. One or more units of rotational fan 750 provide for sufficient airflow to keep the system operational and safe. Rotational fan 750 is aligned with connecting pipes 742, allowing for maximum efficiency.

Figure 17:
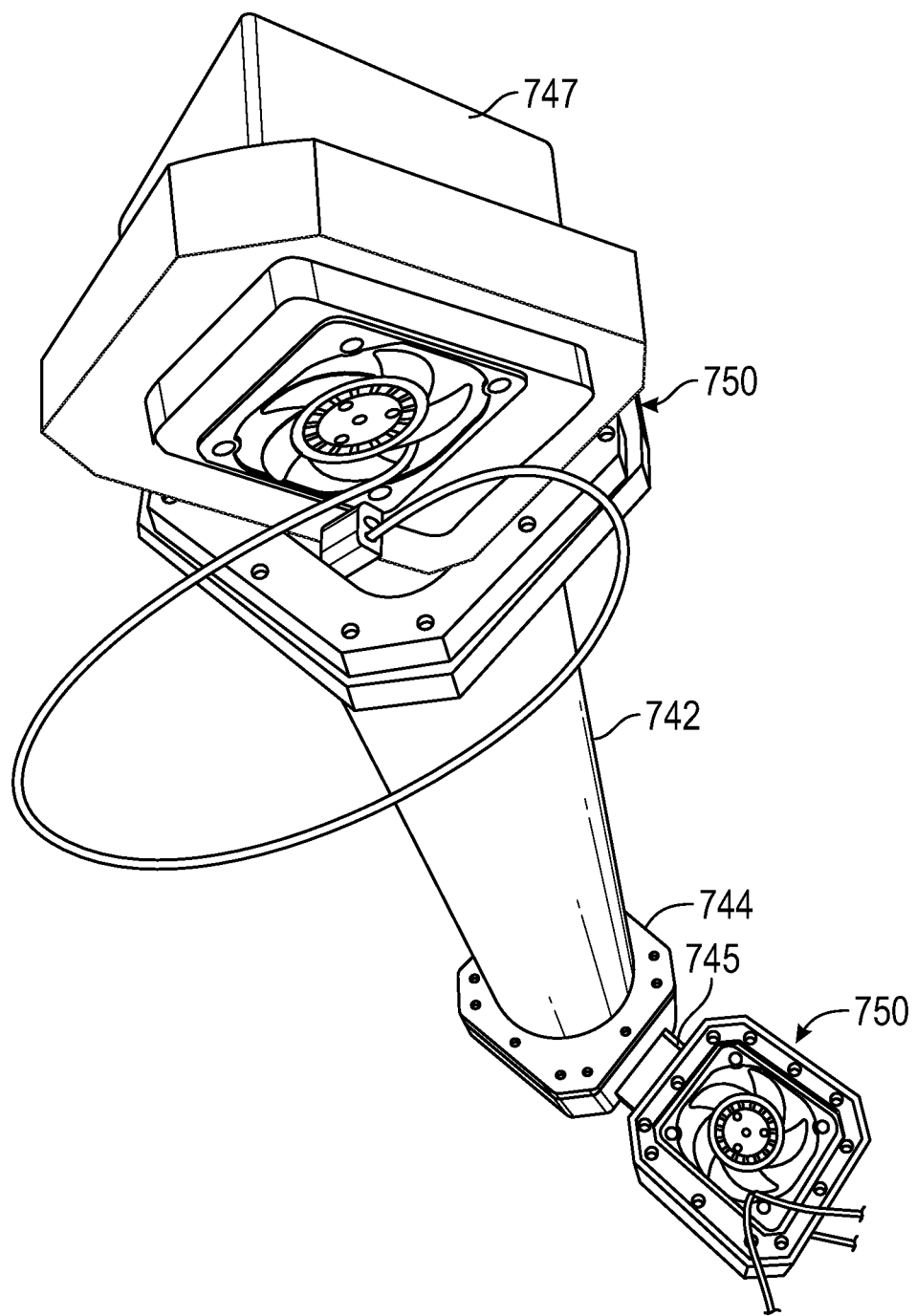
FIG. 17 illustrates an embodiment in which a rotational fan is integrated both into an end mounting bracket and a connecting mounting bracket.

FIG. 17 illustrates an embodiment in which a rotational fan 750 is integrated both into an end mounting bracket 747 and a connecting mounting bracket 744.

Figure 18:
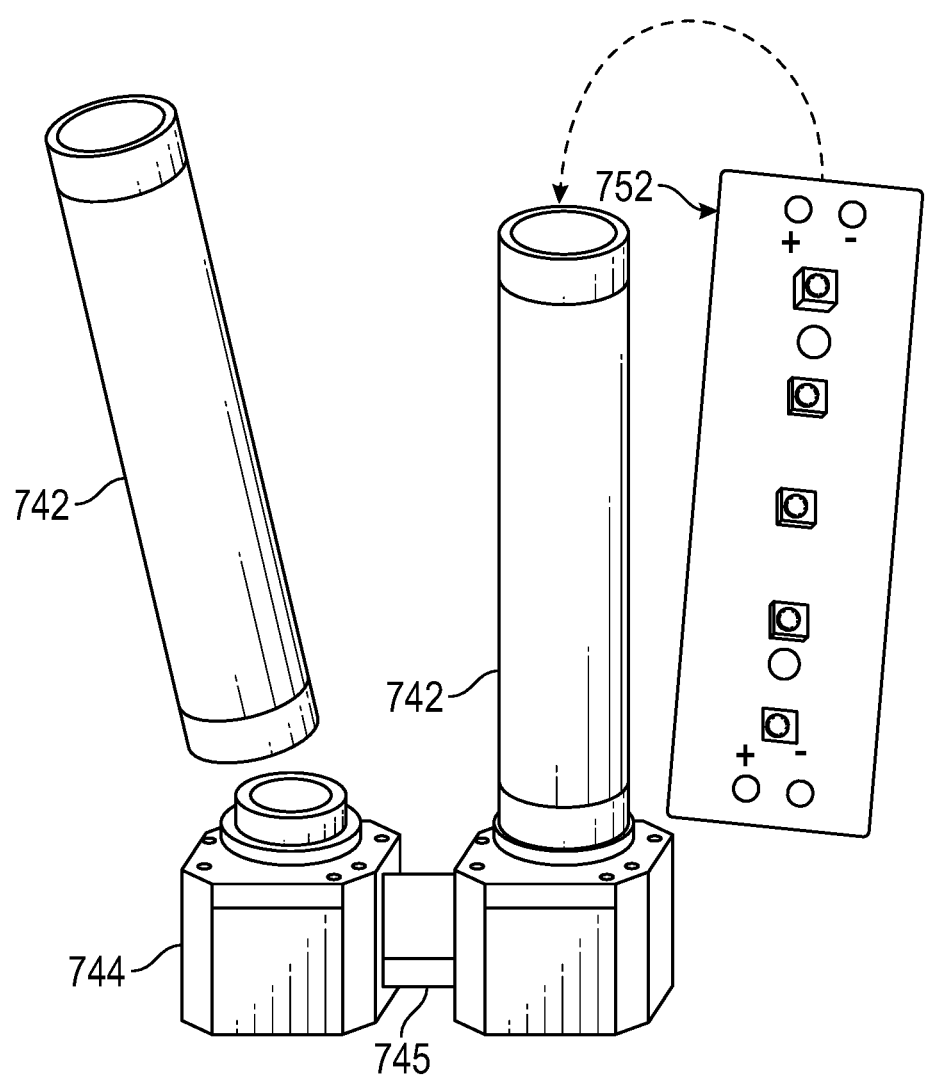
FIG. 18 illustrates an embodiment with a UVC LED strip according to an embodiment of the invention.

FIG. 18 illustrates an embodiment with a UVC LED strip 752 according to an embodiment of the invention. UVC LED strip 752 is inserted into and mounted inside connecting pipes 742 just like any other UVC light source. Some embodiments allow for mounting multiple units of UVC LED strip 752 along the inside surface of connecting pipes 742.

Figure 19:
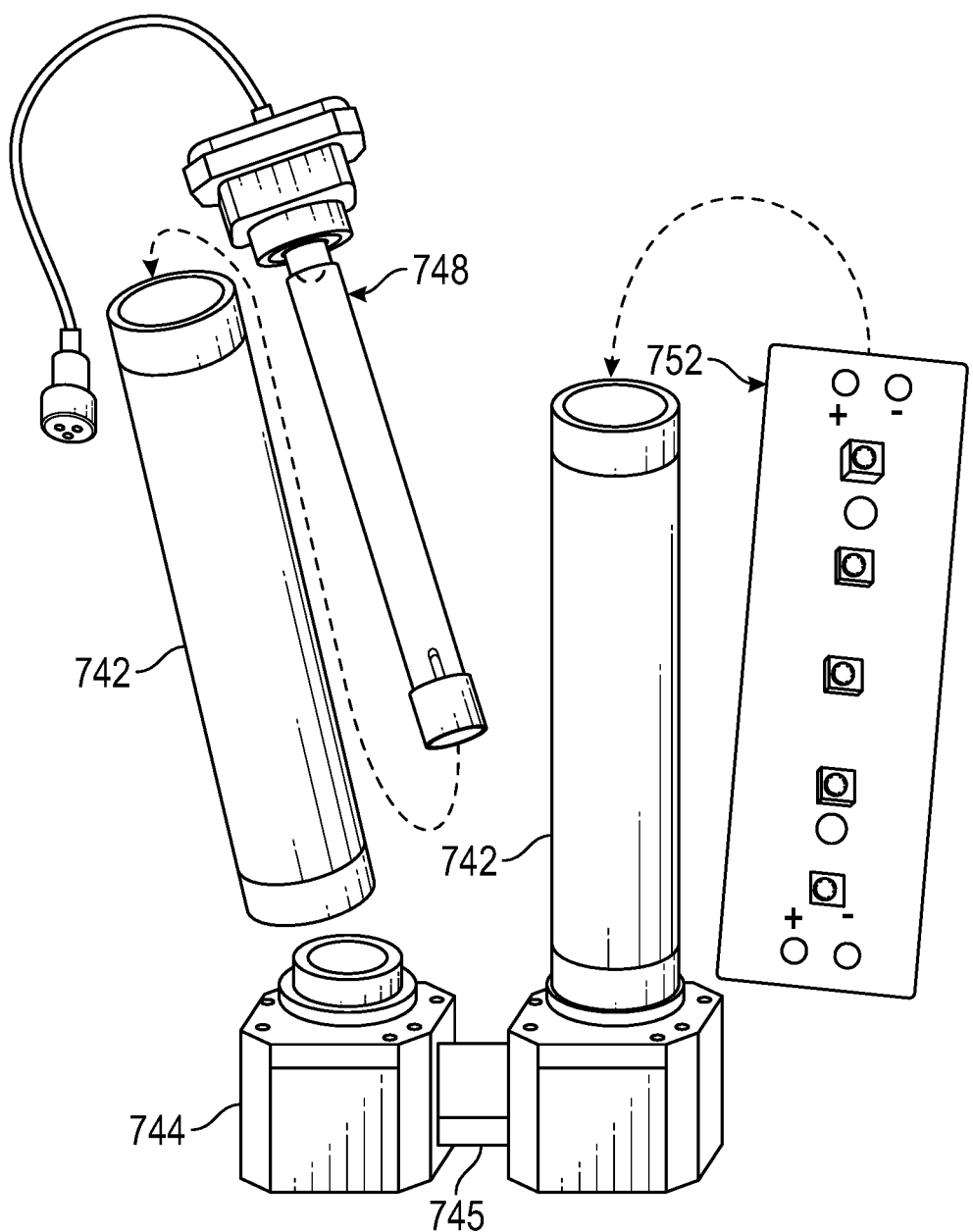
FIG. 19 shows a possible combination of mounting UVC lamps and one or more units of a UVC LED strip in different units of connecting pipes.

FIG. 19 shows the possible combination of mounting UVC lamps 748 and one or more units of UVC LED strip 752 in different units of connecting pipes 742. As mentioned previously, this enables a UVC spectrum optimization for maximum sterilizing efficiency given a known contaminant.

Considerations

Although the description has been described with respect to particular embodiments thereof, these particular embodiments are merely illustrative, and not restrictive. The description may reference specific structural embodiments and methods, and does not intend to limit the technology to the specifically disclosed embodiments and methods. The technology may be practiced using other features, elements, methods and embodiments. Embodiments are described to illustrate the present technology, not to limit its scope, which is defined by the claims. Those of ordinary skill in the art recognize a variety of equivalent variations on the description above.

All features disclosed in the specification, including the claims, abstract, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent, or similar purpose, unless expressly stated otherwise.

It will also be appreciated that one or more of the elements depicted in the drawings/figures can also be implemented in a more separated or integrated manner, or even removed or rendered as inoperable in certain cases, as is useful in accordance with a particular application.

Thus, while particular embodiments have been described herein, latitudes of modification, various changes, and substitutions are intended in the foregoing disclosures, and it will be appreciated that in some instances some features of particular embodiments will be employed without a corresponding use of other features without departing from the scope and spirit as set forth. Therefore, many modifications may be made to adapt a particular situation or material to the essential scope and spirit.

We claim:

1. A wearable device, comprising:
   a headgear;
   an inline system including:
      two end mounting brackets;
      an air inlet filter coupled with one of the end mounting brackets;
      and two or more connecting pipes comprising UVC light sources, wherein two of the two or more connecting pipes are coupled with the two end mounting brackets, and wherein the two or more connecting pipes are configured to receive air from the air inlet filter and to sterilize the air using UVC light from the UVC light sources; and
      a u-shaped backpack coupling two of the two or more connecting pipes and passing the flow of sterilized air from a first of the two connecting pipes to a second of the two connecting pipes, wherein the u-shaped backpack comprises a fan; and
   an air hose coupling the inline system to the headgear and configured to transport a flow of sterilized air from the inline system to the headgear;
   wherein:
   the flow of sterilized air provides an air curtain inside the headgear, flowing from a top of the headgear to a bottom of the headgear, and exiting the headgear at the bottom.

2. The wearable device of claim 1, wherein the u-shaped backpack comprises a bracket to hold one of the UVC light sources.

3. The wearable device of claim 1, wherein one of the two end mounting brackets comprises a bracket to hold one of the UVC light sources.

4. The wearable device of claim 1, wherein the headgear comprises a helmet.

5. The wearable device of claim 1, wherein the headgear comprises a full face mask comprising a sterilized air intake coupled with the air hose, and an air exhaust.

6. The wearable device of claim 1, wherein an inside surface of one of the two or more connecting pipes is lined with reflective material.

7. The wearable device of claim 1, further comprising: a power and electronics pack, including a battery and control electronics to regulate the flow of sterilized air; and a portable display configured to show system information including a battery status.

8. The wearable device of claim 7, wherein the power and electronics pack include a ballast for one of the UVC light sources.

9. The wearable device of claim 1, wherein the inline system includes two belt holders snapped to the two or more connecting pipes and wherein each of the two belt holders has a belt.

10. The wearable device of claim 1, wherein the UVC light sources can be exchanged to optimize a UVC spectrum for any combination of biological contaminants.

11. A wearable device, comprising:
    a headgear;
    an inline system including:
       two end mounting brackets;
       an air inlet filter coupled with one of the end mounting brackets;
       and two or more connecting pipes comprising UVC light sources, wherein two of the two or more connecting pipes are coupled with the two end mounting brackets, and wherein the two or more connecting pipes are configured to receive air from the air inlet filter and to sterilize the air using UVC light from the UVC light sources; and
       two connecting mounting brackets and a bridging bracket, wherein: each of the two connecting mounting brackets couples with one of the connecting pipes; the bridging bracket mechanically couples the two connecting mounting brackets to pass the flow of sterilized air from a first of the connecting pipes to a second of the connecting pipes; and at least one of the two connecting mounting brackets comprises a fan; and
    an air hose coupling the inline system to the headgear and configured to transport a flow of sterilized air from the inline system to the headgear;
    wherein:
    the flow of sterilized air provides an air curtain inside the headgear, flowing from a top of the headgear to a bottom of the headgear, and exiting the headgear at the bottom.

12. The wearable device of claim 11, wherein: at least one of the two connecting mounting brackets comprises a bracket to hold one of the UVC light sources.

13. The wearable device of claim 11, wherein the bridging bracket is divided in two parts, one part on each of the two connecting mounting brackets.

* * * * *